US012768917B2

(12) United States Patent
Biber

(10) Patent No.: US 12,768,917 B2
(45) Date of Patent: Oct. 20, 2026

(54) MAGNETIC RESONANCE IMAGING SYSTEM FOR THE HEAD REGION

(71) Applicant: Siemens Healthineers AG, Forchheim (DE)

(72) Inventor: Stephan Biber, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 19/059,542

(22) Filed: Feb. 21, 2025

(65) Prior Publication Data

US 2025/0271517 A1 Aug. 28, 2025

(30) Foreign Application Priority Data

Feb. 22, 2024 (DE) ..................... 10 2024 201 644.6

(51) Int. Cl.
*G01R 33/34* (2006.01)
*A61B 5/055* (2006.01)

(52) U.S. Cl.
CPC .............. *G01R 33/34* (2013.01); *A61B 5/055* (2013.01)

(58) Field of Classification Search
CPC ................................ G01R 33/34; A61B 5/055
See application file for complete search history.

(56) References Cited

U.S. PATENT DOCUMENTS

| | | | | |
|---|---|---|---|---|
| 2009/0289633 | A1* | 11/2009 | Dutto | G01R 33/3806 324/318 |
| 2012/0146645 | A1 | 6/2012 | Rasche et al. | |
| 2017/0296289 | A1* | 10/2017 | Andrews | A61B 90/10 |
| 2018/0177473 | A1* | 6/2018 | Gregerson | A61B 6/4405 |
| 2022/0308140 | A1* | 9/2022 | Biber | G01R 33/3873 |

FOREIGN PATENT DOCUMENTS

| | | | |
|---|---|---|---|
| DE | 102008009674 | A1 | 8/2009 |
| DE | 102009027119 | A1 | 12/2010 |
| DE | 102021203139 | A1 | 9/2022 |
| JP | 2009162273 | A * | 7/2009 |

* cited by examiner

*Primary Examiner* — Kaitlyn E Sebastian
(74) *Attorney, Agent, or Firm* — Banner & Witcoff, Ltd.

(57) ABSTRACT

A magnetic resonance imaging system may include a scanning unit. The scanning unit may comprise a gantry which has a magnet system with a base field magnet and a patient opening, and a carrier unit which has a vertical translation mechanism which is set up to arrange the gantry in a predetermined height position. Part of the magnetic resonance imaging system may include a patient seat on which a patient can be positioned seated in an at least semi-upright position during imaging and which is arranged to be displaceable in a horizontal direction relative to the gantry.

13 Claims, 7 Drawing Sheets

MAGNETIC RESONANCE IMAGING SYSTEM FOR THE HEAD REGION

CROSS REFERENCE TO RELATED APPLICATIONS

This patent application claims priority to German Patent Application No. 10 2024 201 644.6, filed Feb. 22, 2024, which is incorporated herein by reference in its entirety.

BACKGROUND

Field

The disclosure relates to a magnetic resonance imaging (MRI) system for the head region. In addition, the disclosure relates to a method for configuring a magnetic resonance imaging system.

Related Art

Medical imaging systems, in particular magnetic resonance imaging (MRI) systems, can be used for whole-body imaging as well as for imaging individual regions or parts of the body.

A concept which deals with the most efficient operation of medical imaging systems relates to the use of dedicated medical imaging systems which have a limited scope of application. Such a limited scope of application is, for example, determined by the geometry and the dimensions of the interior of a medical imaging system. If a medical imaging system is only intended to image a certain group of body parts, this can be achieved by restricting the dimensions of the patient opening.

On the other hand, a specific use, in particular of a magnetic resonance imaging system, can also be promoted by a suitable arrangement of a scanning unit of a magnetic resonance imaging system. In particular, for an image of the head or teeth of a patient, it may be favorable to choose a relatively small patient opening and to place the patient in a seated position instead of a reclining position, which is usually more comfortable for the patient and also takes up less space.

Contemporary scanning units of magnetic resonance imaging systems are generally configured in such a way that they generate a horizontally extending base magnetic field (also referred to as a $B_0$-field for short). For this purpose, so-called solenoid magnets are used, which enable a circular opening for the patient. The patient is moved into the circular opening on a patient table and is in a reclining position during the imaging process. However, the space requirement for a universal magnetic resonance imaging system is quite high, so that such systems are usually only found in larger medical facilities, such as hospitals, for example, or facilities specializing in radiology.

In order to reduce X-ray exposure, the use of magnetic resonance imaging as an alternative to X-ray imaging in dentistry as well is being discussed. However, dental practices usually only have limited space and also do not have the financial means to acquire a universal magnetic resonance imaging system.

Consideration is now being given to offering a reduced magnetic resonance imaging system specially designed for dentistry, which is only suitable for imaging of the head region or teeth and due to this specialization has a comparatively small space requirement and can be produced in a relatively resource-saving and therefore also cost-effective manner.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
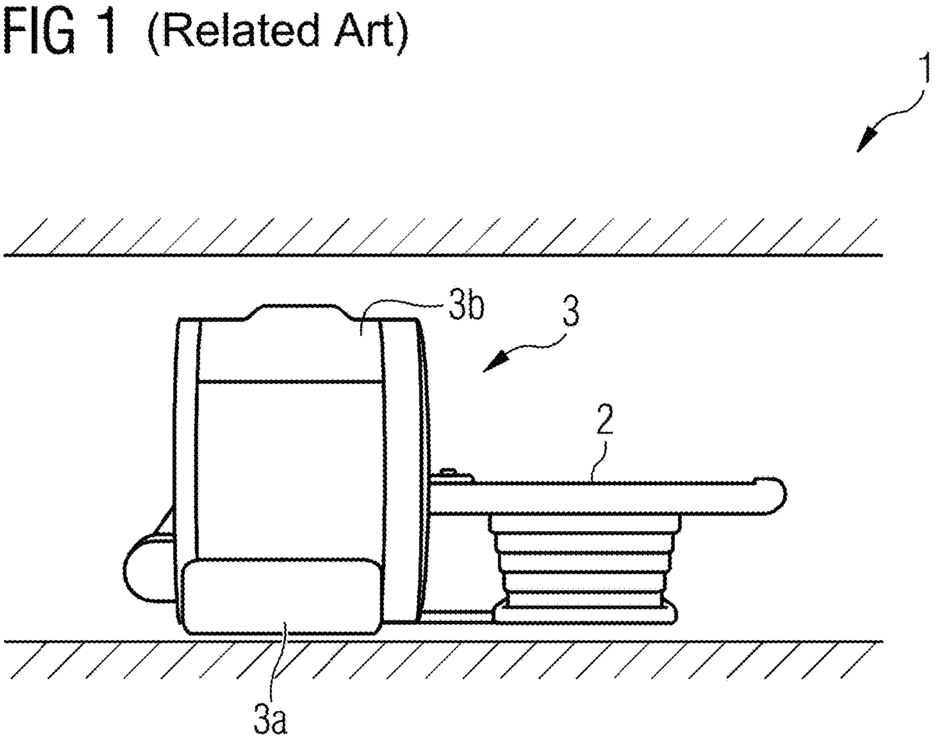
FIG 1 (Related Art)
FIG. 1 is a diagrammatic side view of a conventional magnetic resonance imaging system.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to provide a magnetic resonance imaging system dedicated to head imaging, which is configured to save space and resources and is therefore also suitable for use in individual medical practices, in particular dental practices.

This object is achieved by a magnetic resonance imaging system and by a method for configuring a magnetic resonance imaging system, according to the disclosure.

The magnetic resonance imaging system according to the disclosure has a scanning unit. The scanning unit has a gantry having a magnet system with a base field magnet and a patient opening. Besides the base field magnet, the magnet system may include a gradient coil, a receiver coil and a transmission coil (e.g. a body coil integrated into the gantry and/or a local transmission coil which can be positioned on the patient) and a patient opening. The patient opening is also referred to as the patient receiving area or patient tunnel or bore. A section of the body or the body of a patient is admitted through the gantry. The patient opening is at least partially or completely enclosed by a magnet system along a circumferential direction. The patient opening can be annular, but it can also be designed with a lateral opening.

Part of the scanning unit (scanner) is also a carrier unit (carrier) which has a vertical translation mechanism which is configured to arrange the gantry in a predetermined height position. In particular, the vertical translation mechanism can be designed to arrange the gantry variably and/or in various height positions. In this manner, the height of the gantry can be advantageously adapted to the height or seated position of a patient.

A height position of the gantry may be characterized by a distance of the gantry from a floor surface on which the magnetic resonance imaging system is placed or installed.

The magnetic resonance imaging system according to the disclosure also has a patient seat with an at least semi-upright seated position. The backrest of the patient seat is therefore tilted in such a way that a patient leaning on the backrest on the patient seat can be positioned sitting at least semi-upright before imaging. The patient seat is arranged to be displaceable in a horizontal direction relative to the gantry. “Sitting at least semi-upright” is intended to mean that the patient assumes a seated position and not a reclining position. A reclining position should be understood as a position in which the head of the patient is positioned at the same height as the rest of the body. In a seated position, the head of the patient is elevated relative to the rest of the body, the back is oriented at least diagonally to the floor or even vertically. In order for the head of the patient to enter the (e.g. annular) patient opening for imaging, the patient seat can be moved horizontally in its position and the gantry moved vertically.

The orientation of the gantry can be selected such that the longitudinal axis of the gantry extends vertically, but it can also be selected such that the longitudinal axis of the gantry deviates from the vertical, in particular extends diagonally. As will be explained in detail later, the magnetic resonance imaging system according to the disclosure can also have a swivel mechanism which can be used to switch between different orientations of the gantry.

Advantageously, the patient can be seated in at least partially upright or inclined seated position during imaging. Likewise, advantageously, the height position of the gantry can be adjusted to the height of a seat backrest or the height of a person before imaging. This not only obtains a more comfortable position for the patient, but also reduces the space required for installing the magnetic resonance imaging system. In particular, the space requirement for transporting the gantry is also reduced as it can be quite small in the axial direction and can be moved to the desired examination area before imaging.

In the method according to the disclosure for configuring the magnetic resonance imaging system according to the disclosure, a patient seat on which a patient can be positioned seated in an at least semi-upright position before imaging is set up. Furthermore, a carrier unit having a vertical translation mechanism which arranges a gantry of a scanning unit of the magnetic resonance imaging system in a predetermined height position is set up. The height position of the gantry can be variably adjusted by means of the vertical translation mechanism. Finally, the gantry is connected to the carrier unit in such a way that the gantry of the scanning unit is arranged to be displaceable in a vertical direction so that the head of the patient can be inserted into an annular patient opening of the gantry for imaging or, conversely, the gantry can be pushed over the head of the patient seated below the gantry. The method according to the disclosure shares the advantages of the magnetic resonance imaging system according to the disclosure.

In one embodiment of the magnetic resonance imaging system according to the disclosure, the carrier unit has a swivel mechanism which is configured to swivel the (e.g. annular) gantry about a horizontal swivel axis. Advantageously, the orientation of the gantry can be adapted to the orientation of the head and upper body of a patient sitting on a patient seat. The orientation of the gantry may be selected to conform to the orientation of the backrest of the patient seat. In this position, the head of the patient can be pushed into the patient opening of the gantry by moving the patient seat closer to the scanning unit. While the head of the patient is surrounded by the gantry in this arrangement, the rest of the body of the patient remains outside the gantry. The head of the patient can be pushed into the patient opening due to the inclined seated position of the patient and the inclined arrangement of the gantry, provided that the gantry is arranged at the correct height position, which conforms to the head height of the patient. In order to adjust the height position of the gantry to the head height of the patient, the previously described carrier unit can be used, which has a vertical translation mechanism which is configured to arrange the gantry in a predetermined height position.

In one or more exemplary embodiments of the magnetic resonance imaging system according to the disclosure, the carrier has a locking unit (lock) which is configured to lock the gantry in a desired alignment relative to the horizontal swivel axis. The locking unit may be configured with a positive-locking mechanism for fixing and releasing a swivel position of the gantry. Advantageously, a selected alignment of the gantry can be fixed and thus maintained for the duration of imaging.

The carrier unit may include a swivel angle limiting unit (limiter) which is configured to restrict an angle of rotation of the gantry relative to the horizontal swivel axis. The swivel angle limiting unit may be configured to limit a maximum angle of rotation or swivel angle to a predetermined maximum angle. Excessive swiveling or rotation of the gantry, which could potentially pose a risk of the gantry colliding with the head of a patient, can be advantageously avoided by limiting the possible swivel angle to harmless values.

The swivel mechanism likewise may include an adjustment mechanism for determining a mechanically preset swivel angle, which is achieved by a swivel movement. This presetting allows an assumption of a swivel position by the gantry, which corresponds to a default inclination of a backrest of a patient seat, so that a manual adjustment of the swivel angle of the gantry does not need to be carried out in most cases. An adjustment mechanism may comprise a locking element, a stop element, a clamping element, a latching element, a securing element or the like. In particular, the adjustment mechanism can be designed to limit a movement, e.g. a rotational movement and/or a translational movement, of the gantry along a movement trajectory or rotation path defined by the swivel mechanism.

In an exemplary embodiment, the mechanically preset swivel angle determines an alignment of the longitudinal axis of the gantry in the direction of the longitudinal axis of the upper body of the patient. Advantageously, the patient can be pushed with their head into the patient opening of the gantry by moving their patient seat backwards.

The swivel mechanism may include a ratchet which enables swiveling in a plurality of different predetermined angular increments. Advantageously, the orientation of the gantry can be adapted to different inclinations of the patient seat. In an exemplary embodiment, the predetermined angular increments have a ratchet of one degree, i.e. a gradation of 1°, 2°, 3°, etc. Alternatively, the ratchet may also comprise angular increments smaller or larger than 1 degree.

The swivel mechanism may include one or more of the following types of actuation:

- manual actuation,
- electrical actuation,
- hydraulic actuation.

Manual, purely mechanical actuation is generally particularly reliable and low-maintenance and can be produced with relatively little effort.

Electrical actuation allows automatic adjustment of the inclination of the gantry without the operator having to use muscle power.

Hydraulic actuation is advantageous in particular in the case of a heavy gantry, the hydraulic power transmission allowing particularly high forces and torques and a high power density, in particular compared to the use of an electric motor.

In one embodiment of the magnetic resonance imaging system according to the disclosure, the gantry is designed in such a way that it does not exert any torque which causes a rotation of the gantry relative to the horizontal swivel axis of the swivel mechanism of the scanning unit (scanner) purely due to gravity in the intended arrangement, and thus does not allow the gantry to swivel purely due to gravity. "In the intended arrangement" should mean that the gantry is correctly mounted on the carrier unit, so that in particular the gantry is arranged so that it can swivel about a horizontal swivel axis. Furthermore, the carrier unit is arranged and oriented as intended so that the aforementioned swivel axis for swiveling the gantry is horizontally aligned. This torque-free arrangement is achieved by distributing the weights of the components of the gantry in such a way that no torque is exerted on the swivel axis by these weights without external influence. The components may comprise receiver electronics, magnet electronics, etc. This can be achieved by a weight-symmetrical arrangement of the components of the gantry relative to the swivel axis of the gantry or alternatively by attaching additional balancing weights to the gantry. The swivel mechanism therefore does not allow any swivel movement driven solely by weight force in order to prevent accidents when tilting or swiveling the gantry or the system tipping over.

In one or more exemplary embodiments of the magnetic resonance imaging system according to the disclosure, the carrier unit is designed to be separable from the gantry. "Separable" is intended to mean here that, in particular for transportation, the carrier unit and the gantry can be detached from one another and can be transported as individual elements. As a result of the separability, the carrier unit and the gantry may be reversibly connected to one another. In order to enable a reversible mechanical connection of the magnetic resonance imaging system, the carrier unit and the gantry may have complementary parts of a mechanical connection element. The mechanical connection may be based on a positive and/or non-positive connection of the aforementioned complementary parts. Advantageously, the magnetic resonance imaging system can be transported in individual parts and thus in a space-saving manner, in particular if the gantry, adapted to the size of the head, is comparatively small in size.

The carrier unit may include a base plate with a large area (relative to the cross-section of the support arm unit) and a vertical support arm unit with a small cross-section relative to the area of the base plate. For example, a main surface of the base plate (e.g. a surface of the base plate with the largest dimension) is a multiple, in particular more than tenfold or more than a hundredfold, of the cross-sectional area of a vertical support arm unit. Advantageously, the overall system has good stability due to the large-area base plate, it being possible for the vertical support arm unit to be relatively slim and lightweight and thus, in addition to an elegant appearance, also have a comparatively low transport weight.

In an exemplary embodiment of the magnetic resonance imaging system according to the disclosure, the vertical translation mechanism has a manual drive or a hydraulic drive or an electric drive. The translation mechanism has an adjustment or displacement mechanism with which different relative positions of the gantry in a vertical direction relative to the carrier unit can be controlled and adjusted. If the vertical translation mechanism has a manual drive, it may include threaded rods with which kinetic energy can be introduced manually. In this case, the kinetic energy can be applied by manually turning the threaded rods. If the vertical translation is controlled by a hydraulic drive, the energy can be transferred by hydraulic pumps. Electrical actuation of the translation mechanism with motor support is possible, e.g. by means of a linear drive or an electric motor with a rotating drive principle.

The carrier unit may include a buffer element for vibration decoupling of the gantry from a floor on which the carrier unit is positioned. Advantageously, vibrations caused by the magnetic forces can be damped and the vibrations can be prevented from being transmitted to the floor and in particular the building in which the magnetic resonance system is installed. Such a buffer may comprise one or more springs and/or rubber elements. The vibration decoupling may be arranged in the area of the swivel mechanism or the swivel axis of the swivel mechanism in order to also damp vibrations transmitted to the swivel mechanism.

In one or more exemplary embodiments of the magnetic resonance imaging system according to the disclosure, the gantry is pivotably connected on both sides via its outer side to the carrier unit and relative to the carrier unit. Advantageously, the gantry is supported in a mechanically stable manner.

The carrier unit may be symmetrical to the sagittal plane of the system. A sagittal plane is to be understood as a plane which extends from top to bottom and from back to front. A sagittal plane divides a body into a right and a left part. This symmetry allows particularly good mechanical stability or steadiness of the arrangement.

Likewise, the base plate of the carrier unit may comprise a plurality of subcomponents, dispensing with the need for a continuous base plate and thus saving weight and transportation size.

The base plate of the carrier unit may (additionally) be configured to be separable from the vertical support arm unit of the carrier unit. In this case, the base plate may be configured to be screw-fastened to the support arm unit in order to give the overall system a firm stand. As the overall system can be dismantled, the magnetic resonance imaging system can be transported more easily as it takes up less space when dismantled and the individual elements have a lower weight, making them easier to transport individually than the assembled overall system.

The base plate of the carrier unit may (additionally) comprise buffer elements, such as springs or rubber elements, for vibration decoupling of the magnetic resonance imaging system from the building in which it is installed. Advantageously, it can be achieved that vibrations generated by the magnetic fields of the magnets of the magnetic resonance imaging system, in particular by the gradient fields of the gradient magnets, are sufficiently damped.

The carrier unit may be made of a weakly magnetic or even non-magnetic material.

Advantageously, no magnetic flux from the magnets of the gantry is amplified via the carrier unit and transmitted to the floor of a building.

In an exemplary embodiment, the carrier unit may be made of one or more of the following types of material:

aluminum, non-magnetic steel, stainless steel.

Aluminum is suitable as a particularly lightweight material for transport.

Non-magnetic steel is particularly stable and strong and enables the formation of a carrier unit which is particularly insensitive to vibrations from the gantry. Advantageously, the non-magnetic steel does not transmit any magnetic fields to the outside or, in contrast to a carrier unit made of magnetic material, further amplify them.

Stainless steel is particularly resistant to corrosion.

The above properties can also be combined with one another. The carrier unit may comprise non-magnetic stainless steel, i.e. in particular austenitic or martensitic stainless steel.

FIG. 1 illustrates a diagrammatic side view of a customary magnetic resonance imaging system 1. The customary magnetic resonance imaging system 1 has a patient table 2 on which a patient can sit in a horizontal reclining position. In this reclining position, they are pushed to the left into a patient opening of a gantry 3*b* of a scanning unit (scanner) 3 of the magnetic resonance imaging system 1. The gantry 3*b* is positioned and supported on the floor by a carrier unit (carrier) 3*a*, also referred to as a base. As can be seen in FIG. 1, the dimensions in the length direction and height direction are considerable, so that a correspondingly dimensioned space is required for an examination.

Figure 2:
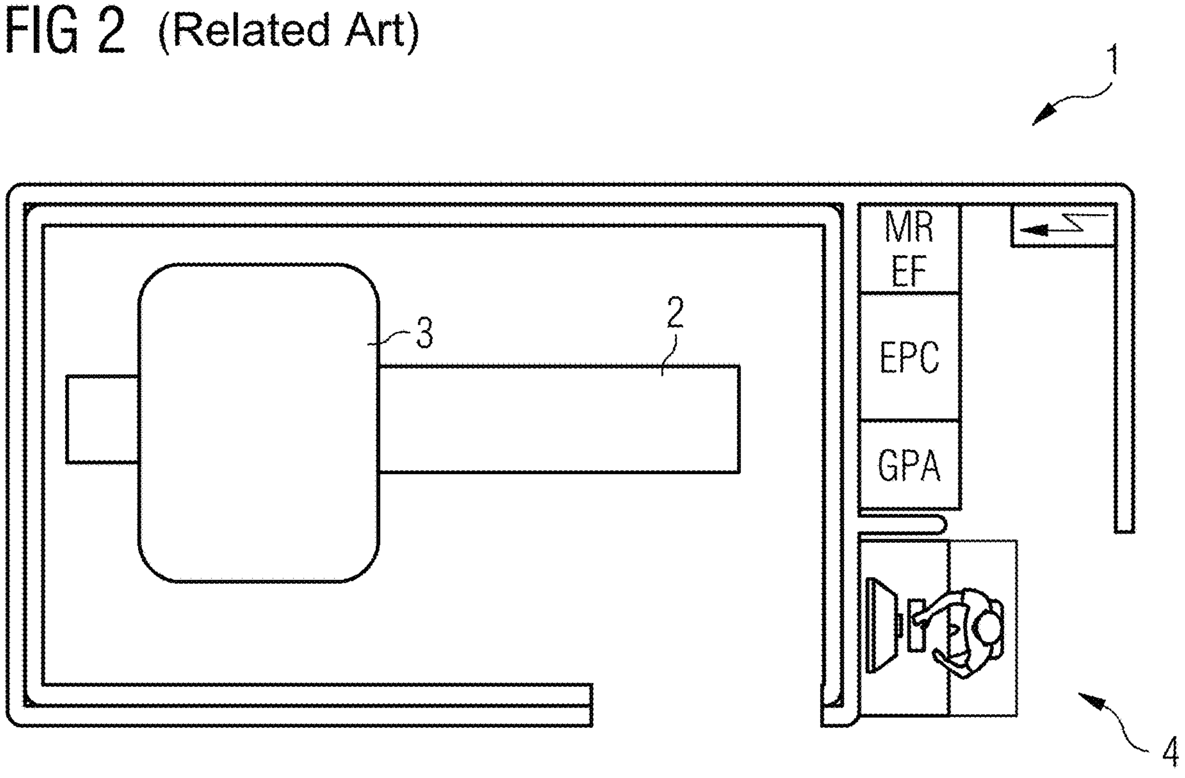
FIG 2 (Related Art)
FIG. 2 is a top view of the magnetic resonance imaging system and an adjacent equipment room illustrated in FIG. 1.

FIG. 2 shows a top view of the customary magnetic resonance imaging system 1 illustrated in FIG. 1 and an adjacent equipment room 4. All electronic components, RF filters and power supplies are housed in the equipment room 4. This is a service area which makes the maintenance of all the electronic devices used in the room easier. Overall, the area for the magnetic resonance imaging system itself requires an area of about 19 $m^2$ and the equipment room 4 has an area of just under 6 $m^2$.

In the equipment room 4, there is also a power amplifier GPA for gradient generation, which is referred to as a Gradient Power Amplifier. Furthermore, in the equipment room 4 there is an electronics cabinet EPC, which is referred to as an Electronics and Power Cabinet. The equipment room 4 also includes a helium compressor for magnetic cooling, which is referred to as Magnet Refrigerator (MREF).

Figure 3:
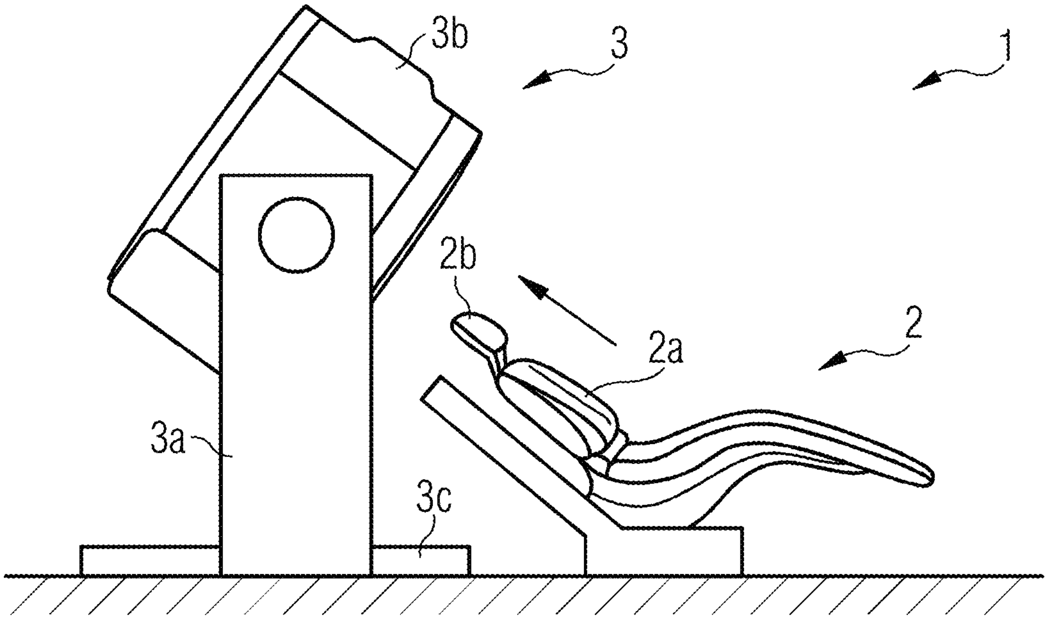
FIG. 3 is a side view of a magnetic resonance imaging system according to an exemplary embodiment of the disclosure.

FIG. 3 shows a side view of a magnetic resonance imaging system 1 according to a first exemplary embodiment of the disclosure. Unlike the customary magnetic resonance imaging system 1, the magnetic resonance imaging system 1 according to a first exemplary embodiment of the disclosure has a patient seat 2 in which a patient can sit in a semi-upright position. The scanning unit 3 is equipped with a pivotable gantry 3*b* to match the patient seat 2, the gantry 3*b* being designed to be pivotable relative to a carrier unit 3*a* on which the gantry 3*b* is mounted. The carrier unit 3*a* also has a base plate 3*c*, which rests on the floor and assumes the functions of a device base. If required, the gantry 3*b* is oriented by the swivel movement in such a way that the alignment of its longitudinal axis conforms to the alignment of the backrest 2*a* of the patient seat 2. If a patient takes a seat on the patient seat 2, the backrest or the headrest area 2*b* of the patient seat 2 can be pushed into the patient opening of the gantry 3*b*. An image of the head region of the patient can then be recorded. In contrast to customary magnetic resonance imaging systems, the patient can adopt their usual seated position, particularly in the field of dentistry, and need not change to a reclining position. In addition, the gantry 3*b* can be dimensioned correspondingly smaller compared to a customary arrangement (see FIG. 1). Overall, this modification greatly reduces the floor space requirement of the magnetic resonance imaging system 1, as illustrated in FIG. 4.

Figure 4:
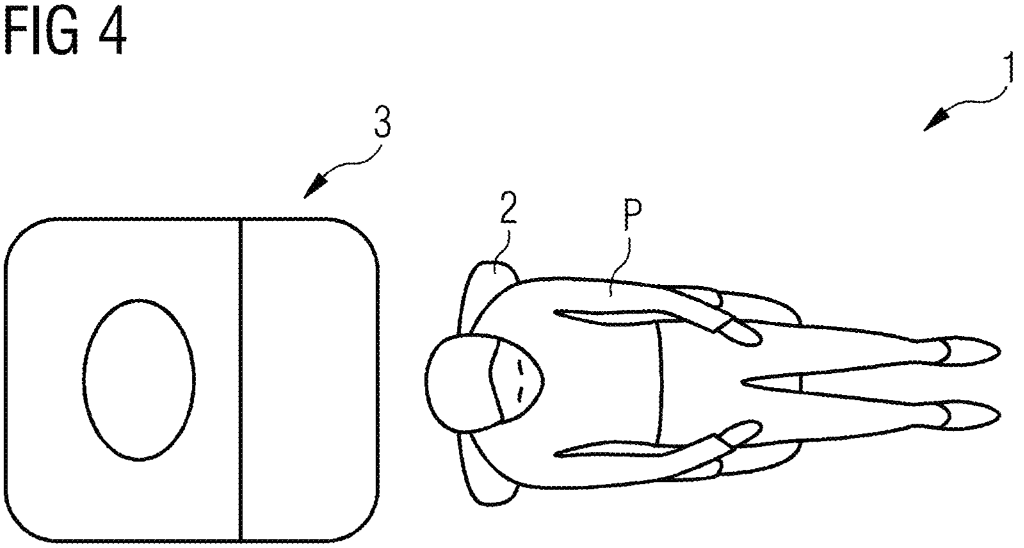
FIG. 4 is a top view of the magnetic resonance imaging system according to an exemplary embodiment of the disclosure illustrated in FIG. 3.

FIG. 4 shows a top view of the magnetic resonance imaging system 1 according to an exemplary embodiment of the disclosure illustrated in FIG. 3. As can be seen in FIG. 4, the space requirement for the examination room is reduced due to the reduced linear expansion of the magnetic resonance imaging system 1 and the patient seat 2. The space requirement of the arrangement according to the disclosure is typically about 8 to 9 $m^2$, which means approximately halving the space requirement compared to the corresponding customary arrangement (19 $m^2$).

Figure 5:
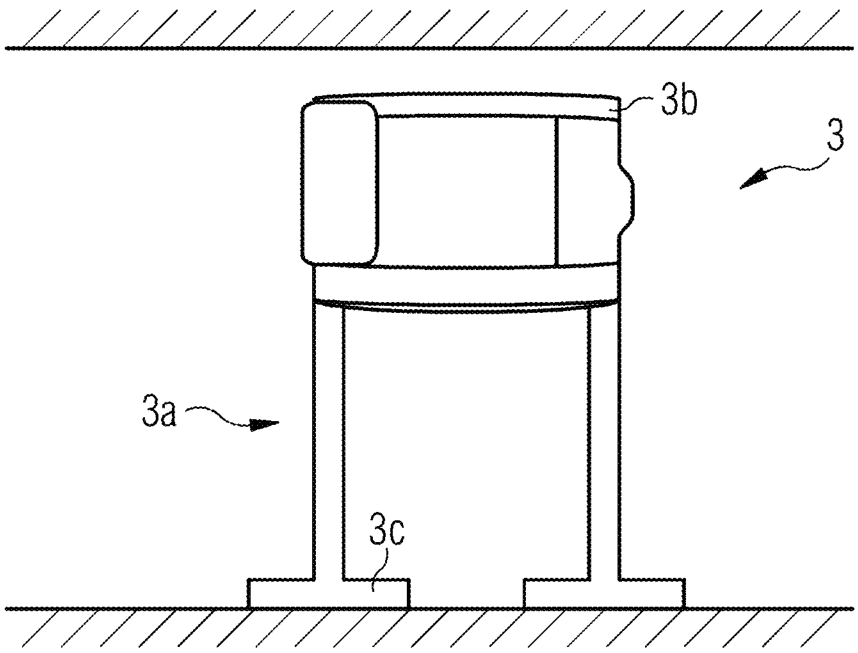
FIG. 5 is a side view of a magnetic resonance imaging system according to an alternative exemplary embodiment of the disclosure.

FIG. 5 shows a side view of a scanning unit 3 of a magnetic resonance imaging system according to an alternative exemplary embodiment of the disclosure. Unlike the exemplary embodiment illustrated in FIG. 3 and FIG. 4, the gantry 3*b* shown in FIG. 5 is not designed to be pivotable. Instead, the height position of the gantry 3*b* can be adjusted as required. For this purpose, the gantry 3*b* has guide elements (not shown in FIG. 5), which can slide up and down along the support rails of the carrier unit 3*a*.

Figure 6:
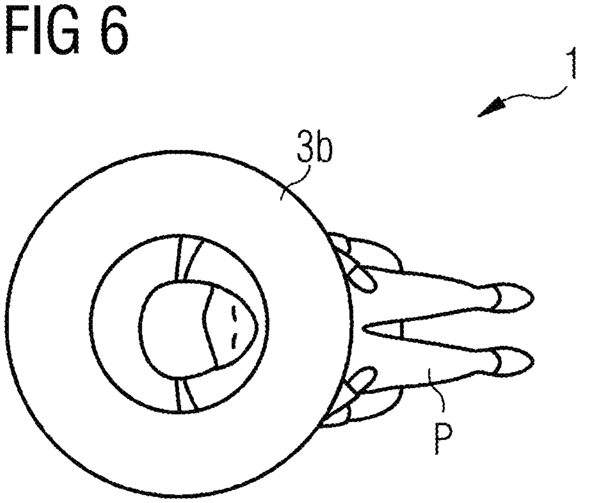
FIG. 6 is a top view of the magnetic resonance imaging system already illustrated in FIG. 5.

As illustrated in FIG. 6, a top view of the magnetic resonance imaging system 1 associated with the scanning unit 3 already illustrated in FIG. 5 shows that a patient can sit under the gantry 3*b* in an upright seated position on a patient seat with an upright backrest. The gantry 3*b* is then moved downwards and positioned at the height of the head of the patient in order to record an image of the head region of the patient, for example their jaw area.

Figure 7:
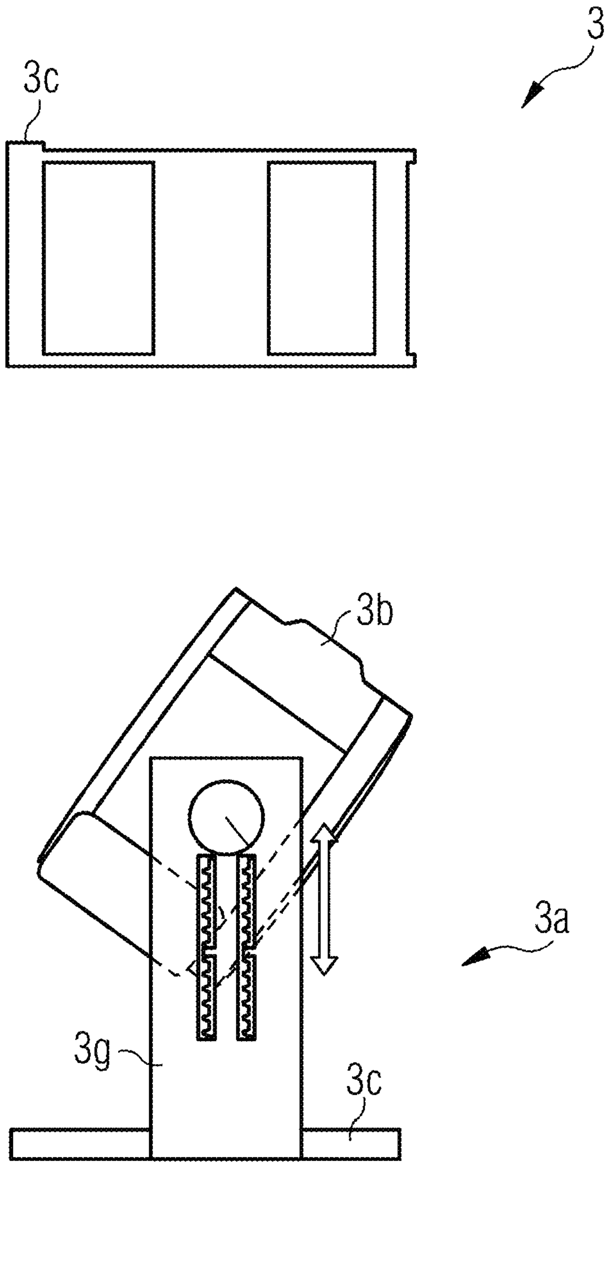
FIG. 7 is a top view of a base plate and a side view of a swivel mechanism of the magnetic resonance imaging system according to an exemplary embodiment of the disclosure illustrated in FIG. 3 and FIG. 4.

FIG. 7 shows a top view of a base plate 3*c* and a side view of a swivel mechanism of the scanning unit 3 of the magnetic resonance imaging system 1 according to a first exemplary embodiment of the disclosure illustrated in FIG. 3 and FIG. 4. The base plate 3*c* has recesses in which the carrier elements 3*g* of the carrier unit 3*a* can be fixed. An adjustment and swivel unit is arranged on the carrier elements 3*g*, with which the gantry 3*b* can be swiveled about a transverse axis and moved in a vertical direction.

Figure 8:
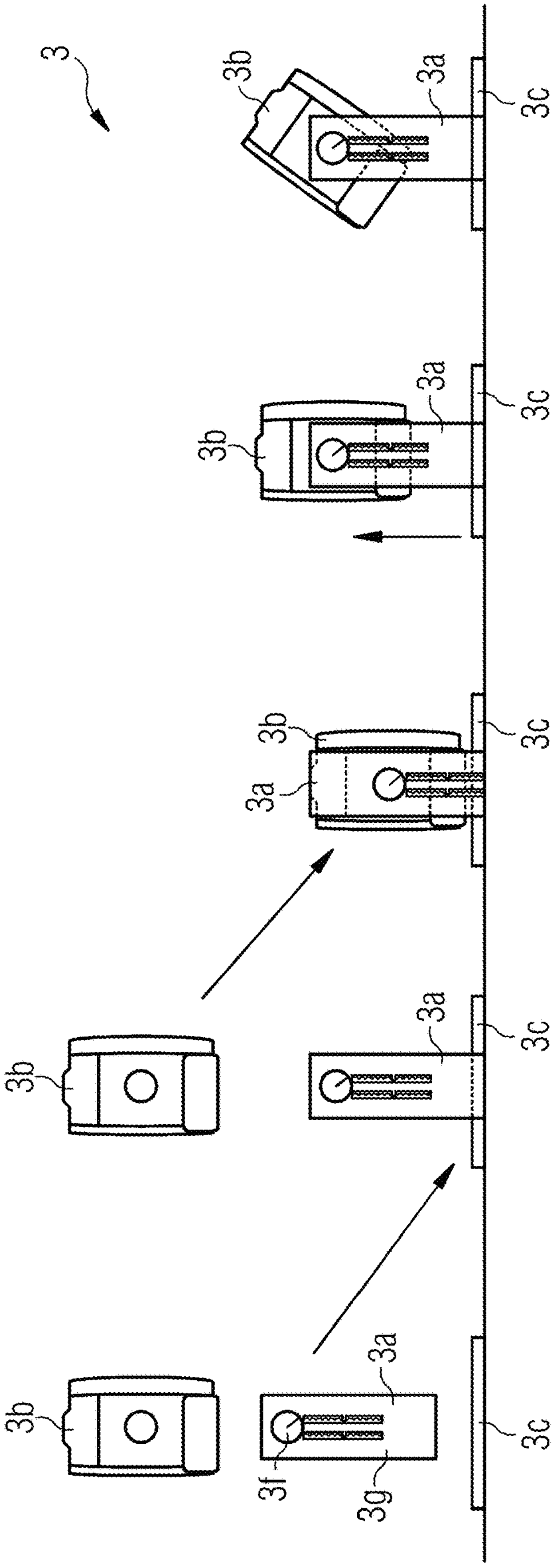
FIG. 8 is a side view which illustrates an assembly of the magnetic resonance imaging system shown in FIG. 3 and FIG. 4 as well as FIG. 7 according to an exemplary embodiment of the disclosure.

FIG. 8 shows a side view which illustrates an assembly of the gantry 3 of a magnetic resonance imaging system 1 according to an exemplary embodiment of the disclosure shown in FIG. 3 and FIG. 4 as well as FIG. 7. Hereinafter, the five partial images shown in FIG. 8 are explained in order from left to right. The first partial image shows the individual components of the magnetic resonance imaging system 1 according to an exemplary embodiment of the disclosure, i.e. the gantry 3*b*, the carrier unit 3*a* with two carrier elements 3*g* and the base plate 3*c* arranged one above the other.

The second partial image shows how the carrier elements 3*g* of the carrier unit 3*a* are attached to the base plate 3.

Subsequently, the third partial image shows that the gantry 3*b* is suspended between the carrier elements 3*g* by means of a pivot bearing 3*f*.

The fourth partial image shows how the gantry 3*b* is moved upwards to a desired height position. In doing so, the gantry 3*b* or its suspension slides upwards guided by the vertical grooves shown.

Finally, the gantry 3*b* is swiveled into a desired position, as shown in the fifth partial image on the far right, so that a patient seated on a patient seat with an inclined backrest can be pushed with their head into the patient opening of the gantry 3*b*.

Figure 9:
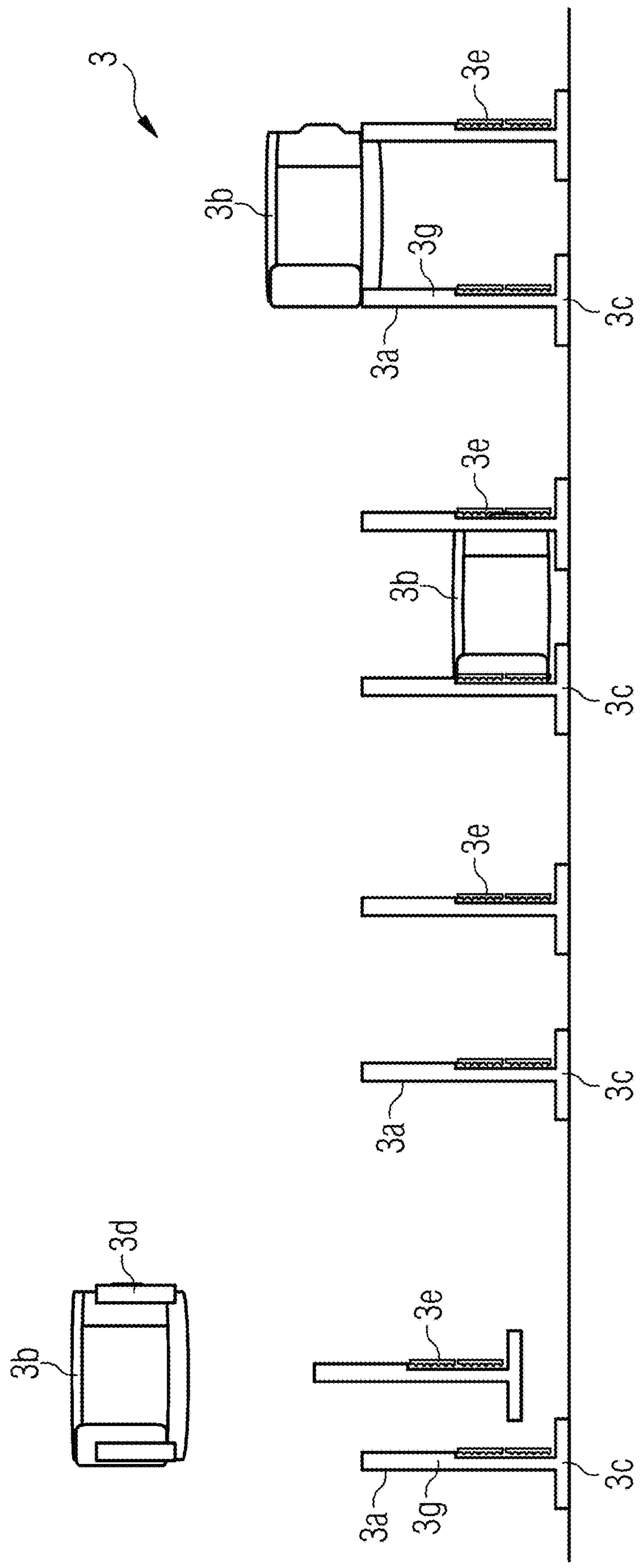
FIG. 9 is a side view which illustrates an assembly of the magnetic resonance imaging system according to an alternative exemplary embodiment of the disclosure shown in FIG. 5 and FIG. 6.

FIG. 9 shows a side view which illustrates an assembly of the scanning unit 3 for a magnetic resonance imaging system according to an alternative exemplary embodiment of the disclosure shown in FIG. 5 and FIG. 6. The carrier elements 3*g* of the carrier unit 3*a* of the scanning unit 3 have guide rails 3*e* on which a holder 3*d* of the gantry 3*b* of the scanning unit 3 can slide. The third partial image from the left shows the positioning of the gantry 3*b*, the gantry 3*b* being arranged in the area of the guide rails 3*e* facing the base plate 3*c* of the scanning unit 3. In this position, the scanning unit 3 takes up little space, this position therefore being particularly suitable for transporting the scanning unit 3. As can be seen in the partial image on the right in FIG. 9, the gantry 3*b* can be slid into an upper position on the carrier elements 3*g* so that a patient can sit upright underneath it.

Figure 10:
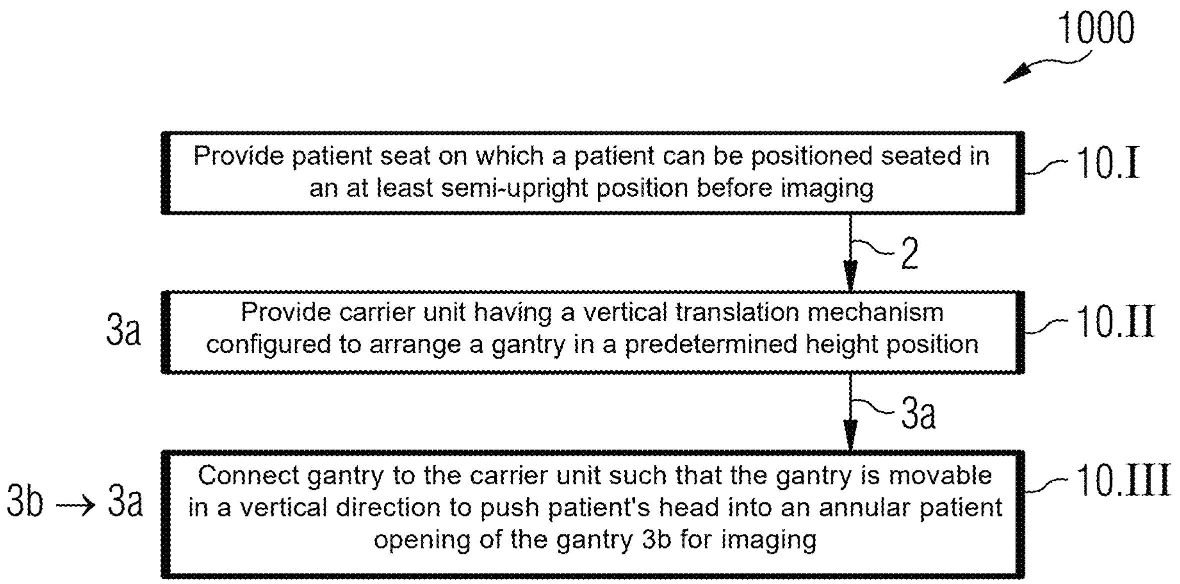
FIG. 10 is a flowchart of a method for configuring a magnetic resonance imaging system according to an exemplary embodiment of the disclosure.

FIG. 10 shows a flow chart 1000 which illustrates a method for configuring a magnetic resonance imaging system 1 according to an exemplary embodiment of the disclosure.

In step 10.I, a patient seat 2 is set up on which a patient can be positioned seated in an at least semi-upright position before imaging.

In step 10.II, a carrier unit 3*a* is set up which has a vertical translation mechanism which is configured to arrange a gantry 3*b* of a scanning unit 3 of the magnetic resonance imaging system 1 in a predetermined height position.

In step 10.III, the gantry 3*b* is connected to the carrier unit 3*a* in such a way that the gantry 3*b* of the scanning unit 3 can be moved in a vertical direction so that the head of the patient P can be pushed into an annular patient opening of the gantry 3*b* for imaging.

Finally, it is pointed out once again that the methods and apparatuses described above are merely exemplary embodiments of the disclosure and that the disclosure can be varied by a person skilled in the art without departing from the scope of the disclosure, insofar as it is specified by the claims. For the sake of completeness, it is also pointed out that the use of the indefinite article “a” or “an” does not exclude the possibility that the relevant features may be present more than once. Likewise, the term “unit” does not exclude the possibility that it consists of several components, which may also be spatially distributed. Independent of the grammatical term usage, individuals with male, female or other gender identities are included within the term.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms “first”, “second”, etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms “comprise” and “have” and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to “one embodiment,” “an embodiment,” “an exemplary embodiment,” etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," or "devices." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, units, or devices, as applicable and relevant, may alternatively be referred to herein as "circuitry," "controllers," "processors," or "processing circuitry," or alternatively as noted herein.

The invention claimed is:

1. A magnetic resonance imaging system, comprising:
- a scanner comprising:
  - a gantry including a magnet system with a base field magnet and a patient opening;
  - a carrier having a vertical translation mechanism configured to arrange the gantry in a predetermined vertical position, wherein the carrier is configured to be separable from the gantry; and
- a patient seat on which a patient is positionably seatable in an at least semi-upright position during imaging and which is configured to be displaceable in a horizontal direction relative to the gantry.

2. The magnetic resonance imaging system as claimed in claim 1, wherein the carrier has a swivel mechanism configured to swivel the gantry about a horizontal swivel axis.

3. The magnetic resonance imaging system as claimed in claim 2, wherein the carrier has a lock configured to lock the gantry in a desired alignment relative to the horizontal swivel axis.

4. The magnetic resonance imaging system as claimed in claim 2, wherein the carrier has a swivel angle limiter configured to limit an angle of rotation of the gantry relative to the horizontal swivel axis.

5. The magnetic resonance imaging system as claimed in claim 2, wherein the swivel mechanism has an adjustment mechanism configured to define a mechanically preset swivel angle, which is achieved by a swivel movement.

6. The magnetic resonance imaging system as claimed in claim 5, wherein, at the mechanically preset swivel angle, a longitudinal axis of the gantry is aligned in a direction of the longitudinal axis of an upper body of the patient.

7. The magnetic resonance imaging system as claimed in claim 2, wherein the swivel mechanism includes a ratchet configured to enable the gantry to be pivoted in a plurality of different predetermined angular increments.

8. The magnetic resonance imaging system as claimed in claim 2, wherein the swivel mechanism comprises: manual actuation, electrical actuation, and/or hydraulic actuation.

9. The magnetic resonance imaging system as claimed in claim 2, wherein the gantry is configured such that the gantry avoids an exertion of torque that causes a rotation of the gantry relative to the horizontal swivel axis of the swivel mechanism due to gravity alone in an intended arrangement.

10. The magnetic resonance imaging system as claimed in claim 1, wherein the carrier includes a base plate and vertical carriers having a smaller cross-section as compared to an area of the base plate.

11. The magnetic resonance imaging system as claimed in claim 1, wherein the vertical translation mechanism comprises: a manual drive, a hydraulic drive, and/or an electric drive.

12. The magnetic resonance imaging system as claimed in claim 1, wherein the carrier includes a buffer configured to vibrationally isolate the gantry from a floor on which the carrier is positionable.

13. A method for configuring a magnetic resonance imaging system, comprising:
- providing a patient seat on which a patient is positionably seatable in an at least a semi-upright position before imaging;
- providing a carrier including a vertical translation mechanism for arranging a gantry of a scanner of the magnetic resonance imaging system in a predetermined vertical position, the carrier being separable from the gantry; and
- connecting the gantry to the carrier such that the gantry of the scanner is displaceable in a vertical direction so that a head of the patient is insertable into a patient opening of the gantry for imaging.

* * * * *